(12) United States Patent
Erni et al.

(10) Patent No.: US 6,599,264 B1
(45) Date of Patent: Jul. 29, 2003

(54) METHOD AND SYSTEM FOR ADMINISTERING A MEDICATION

(75) Inventors: Werner Erni, Therwill (CH); Martin List, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/491,155

(22) Filed: Jan. 26, 2000

(30) Foreign Application Priority Data

Feb. 26, 1999 (EP) ............................................ 99810168
Jul. 2, 1999 (EP) ............................................ 99810580

(51) Int. Cl.[7] ........................ A61M 37/00; A61M 5/30; A61M 5/00; A61M 25/16; A61B 17/43
(52) U.S. Cl. ............................. 604/68; 604/82; 604/83; 604/87; 604/88; 604/91; 604/533; 604/538; 604/905; 604/89; 604/90; 604/232; 604/72
(58) Field of Search ........................... 604/68, 232, 72, 604/82–91, 140, 905, 403, 439, 533, 538; 141/27, 329; 68/141

(56) References Cited

U.S. PATENT DOCUMENTS

| | | |
|---|---|---|
| 4,338,980 A | 7/1982 | Schwebel et al. |
| 4,913,699 A * | 4/1990 | Parsons .......................... 604/68 |

FOREIGN PATENT DOCUMENTS

| | | |
|---|---|---|
| EP | 2762990 | 11/1998 |
| WO | WO 89/08469 | 9/1989 |
| WO | WO 96/19252 | 6/1996 |
| WO | WO 97/38744 | 10/1997 |

OTHER PUBLICATIONS

Weston, Filling device for a needleless injector cartridge, U.S. patent application Publication No. US2000/0051793, Publication Date Dec. 13, 2001.*
Weston, Needleless injector cartridgge, US Patent Pub No. 2001/0027290, Oct. 4, 2001.*
Weston, Filling Device for a Needleless Injector Cartridge, US Patent No. 2001/0051793, Dec. 13, 2001.*
Weston et al, Method of Filling a Drug capsule and Article Produced Thereby, US Patent Pub No. 2002/0128595, Sep. 12, 2002.*

* cited by examiner

Primary Examiner—Michael J. Hayes
Assistant Examiner—Roz Ghafoorian
(74) Attorney, Agent, or Firm—George W. Johnston; Patricia S. Rocha-Tramaloni; Lyman H. Smith

(57) ABSTRACT

A method and a needleless injection system for administering a medication. In order to simplify as far as possible the handling necessary for loading the injector with medication and thereby eliminate risks caused by a complex handling the method and system according to the invention provide loading of medication into a needleless injector device by means of a syringe prefilled with a medication, this loading step preferably including connecting the syringe to the injector device by means of a suitable coupling member or adapter and operating the syringe for transferring medication prefilled therein into the injector device. After this transfer the syringe and/or the coupling member or adapter are detached from the injector device, which is then ready to be operated for ejecting the loaded dosage of said medication from the injector device and thereby pass the selected dosage through the skin of an injection receiver.

14 Claims, 4 Drawing Sheets

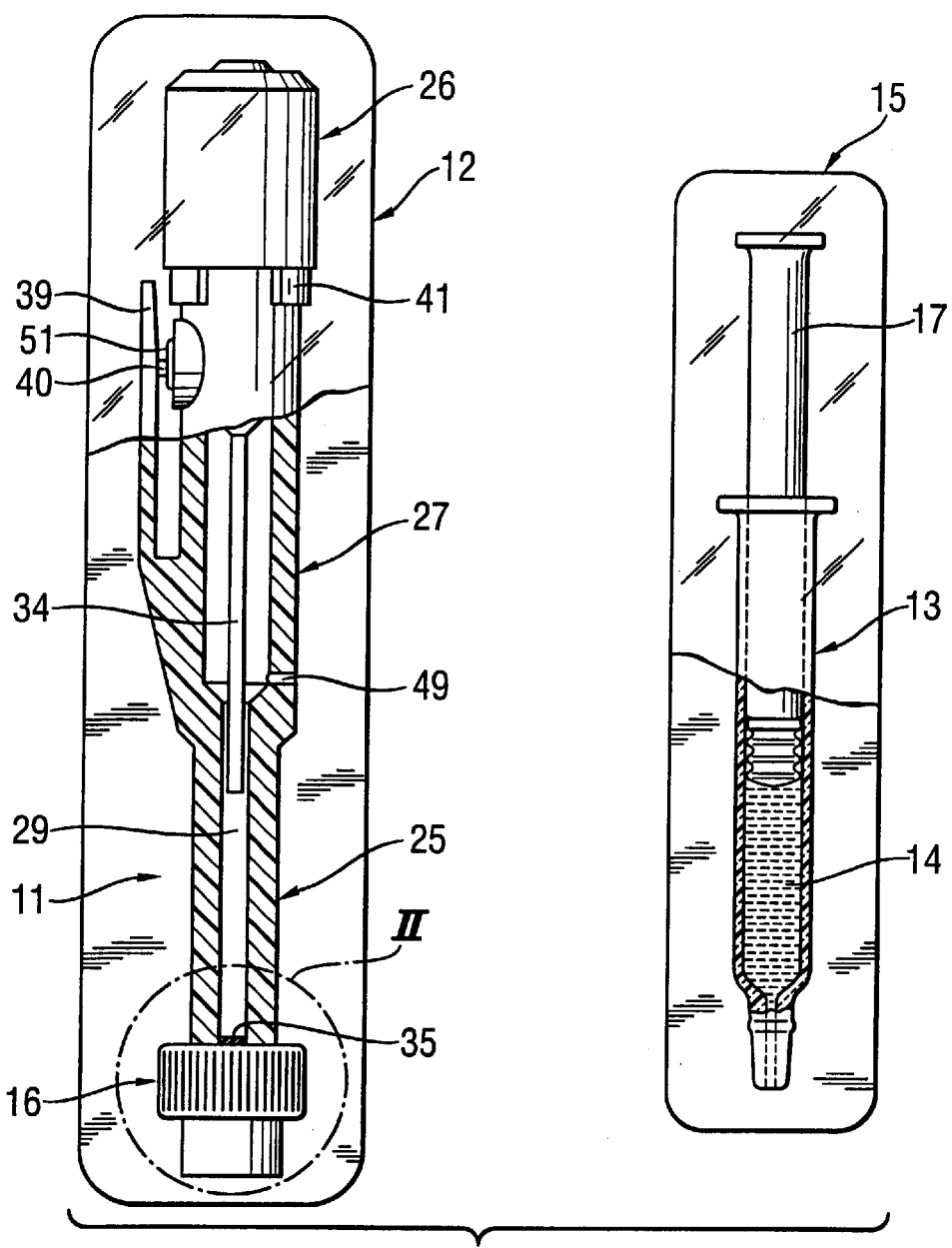
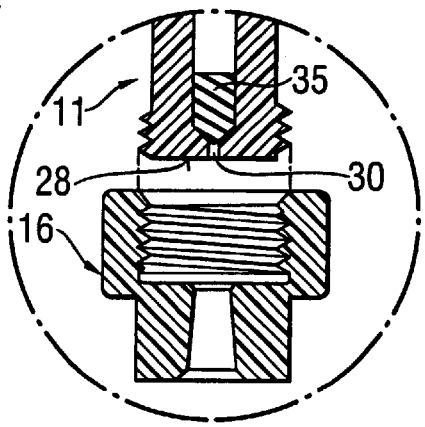
Fig. 1
Fig. 2

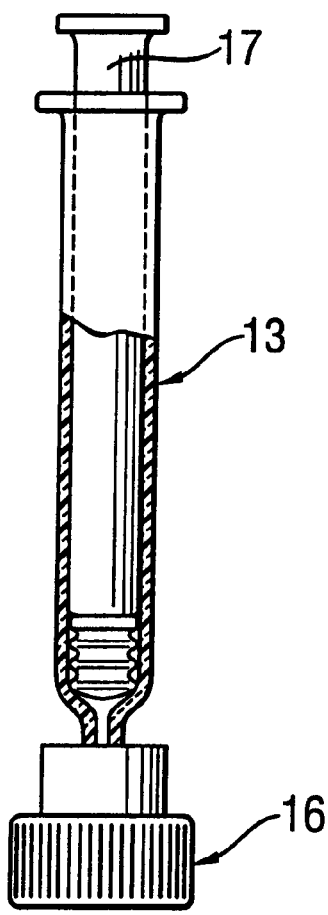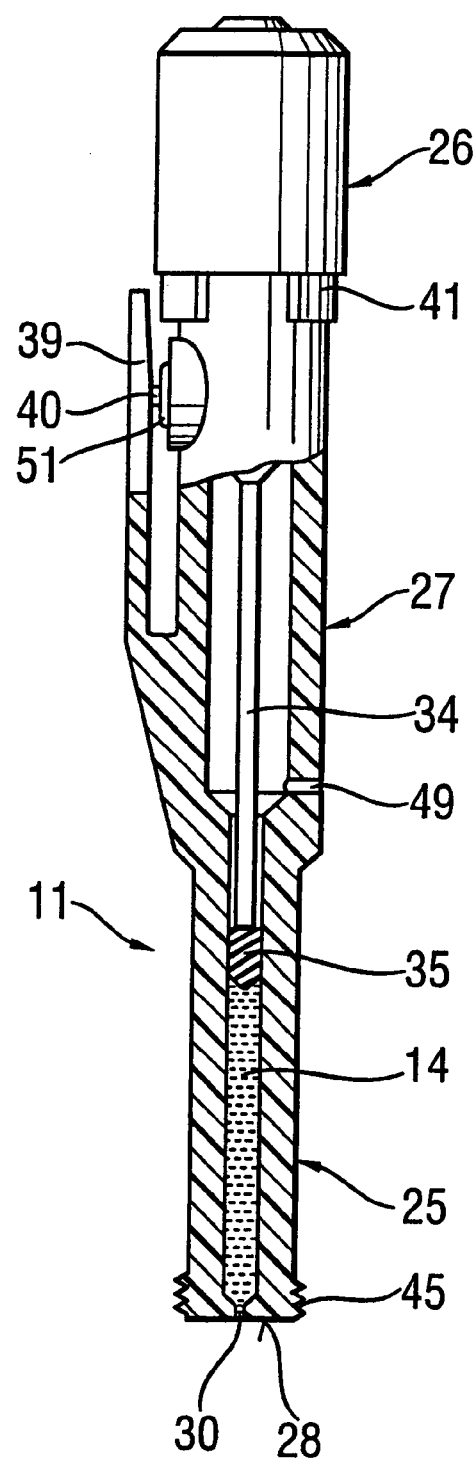

METHOD AND SYSTEM FOR ADMINISTERING A MEDICATION

FIELD OF THE INVENTION

The invention concerns a method for parenterally administering a medication.

The invention also concerns a needleless injection system for administering a medication.

The invention also concerns a coupling member and a kit suitable for performing a method according to the invention.

BACKGROUND

The International Patent Application published under No. WO 89/08469 describes a method and a system of the above mentioned kind. This known system comprises a needleless injector device, a vial coupler device and a transporter/loader device. The method of use of this known system comprises the following steps:

In a first step, one end of the vial coupler device has to be connected to a vial containing the medication to be administered, and this includes piercing a piercable closure of the vial with a cannula forming part of the vial coupler device.

In a second step, the opposite end of the vial coupler device has to be connected to the transporter/loader device in order to establish a fluidic connection between the interior of the vial and the interior of the transporter/loader device.

In a third step, the transporter/loader device has to be operated for transferring a certain amount of medication from the vial into the transporter/loader device, said amount passing through the vial coupler device.

In a fourth step the transporter/loader device has to be disconnected from the vial coupler and connected to the needleless injector device for transferring a certain amount of medication from the transporter/loader device to the needleless injector device.

In a fifth step the transporter/loader device has to be disconnected from the needleless injector device. Only after completion of this step is the needleless injector device ready for the intended use, that is, for administering the medication.

From the foregoing description of the method of use of the device described in the International Patent Application WO 89/08469, it can appreciated that these known method and system have the serious disadvantage that their use requires a complicated handling comprising several steps, and that corresponding risks result therefrom, in particular the risk of microbial contamination during the handling. Also misdosing (inaccurate amount of medication) is likely to occur.

SUMMARY OF THE INVENTION

The aim of the invention is therefore to provide a method and system for administering a medication and a needleless injection system which eliminate the above mentioned disadvantages, that is, to provide a method and system which make possible to load a needleless injection system with a minimum of handling, and thereby preventing the above mentioned risks.

According to a first aspect of the invention this aim is attained with a coupling member comprising:
(a) a first end configured and dimensioned to correspond to the shape of a discharge end of an needless injector device;
(b) a second end configured and dimensioned to correspond to and receive a luer tip of a syringe; and
(c) an inner surface configured and dimensioned to establish a fluidic communication between an interior portion of the needleless injector device and an interior portion of the syringe.

According to a second aspect of the invention this aim is attained with a kit comprising:
(a) a needleless injector device;
(b) a syringe having a luer tip; and
(c) a coupling member comprising:
   (i) a first end configured and dimensioned to correspond to the shape of a discharge end of the needless injector device;
   (ii) a second end configured and dimensioned to correspond to and receive the luer tip of the syringe; and
   (iii) an inner surface configured and dimensioned to establish a fluidic communication between an interior portion of the needleless injector device and an interior portion of the syringe.

According to a third aspect of the invention this aim is attained with a method for parenterally administering a medication, comprising:
(a) providing a needleless injector device having a barrel portion, a gas storage portion, and an intermediate portion extending between the barrel portion and the gas storage portion;
(b) providing a syringe prefilled with a medication said syringe being suitable for needleless loading of the injector device with said medication prefilled in the syringe;
(c) loading t he medication prefilled in the syringe into a bore of the barrel portion of the injector device through an aperture in the barrel portion thereof;
(d) detaching the prefilled syringe from the injector device; and
(e) operating the loaded injector device to eject the dosage of medication contained there in from the injector device and thereby pass said dosage of the medication through the skin of an injection receiver.

According to a fourth aspect of the invention this aim is attained with a needleless injection system, comprising:
(a) a needleless injector device that is dimensioned and arranged as an integral unit to be grasped in the hand of a user, the device having a barrel portion, a gas storage portion, and an intermediate portion extending between the barrel portion and the gas storage portion; and
(b) a syringe prefilled with a medication, said syringe being suitable for loading the injector device with said medication prefilled in the syringe.

In a preferred embodiment such a system further comprises coupling means for connecting the prefilled syringe to the needleless injector device and thereby establishing a fluidic communication between the interior of the syringe and the interior of the injector device for the purpose of transferring a quantity of medication from the prefilled syringe into the needleless injector device.

The main advantage of the invention is that it makes possible a completely needleless loading of the needleless injector device with medication prefilled in the syringe in a most simple way which requires a minimum of handling and therefore prevents risks resulting from complicate handling necessary with prior art devices and methods.

BRIEF DESCRIPTION OF THE DRAWINGS

Preferred embodiments of the invention are described hereinafter with reference to the accompanying drawings wherein:

FIG. 1 shows a schematic representation of the components of a preferred embodiment of a needleless injection system according to the invention, FIG. 2 shows separately the end part of the injector device 11 in FIG. 1 and a coupling member 16, which is suitable for connecting that end part to the syringe 13 in FIG. 1, FIG. 5 shows the syringe 13 and the coupling member 16 connected thereto after they have been detached from the injector device 11 after the transfer of the medication from the syringe into the injector device 11, FIG. 6 shows the injector device 11 ready for use after it has been loaded with the medication and has been detached from the coupling member 16 and the syringe 13 connected thereto.

FIG. 8 shows an enlarged cross sectional view of the injector device taken on line 2—2 of FIG. 7 with the device loaded and ready for firing, but with the safety on.

DETAILED DESCRIPTION OF THE INVENTION

Figure 3:
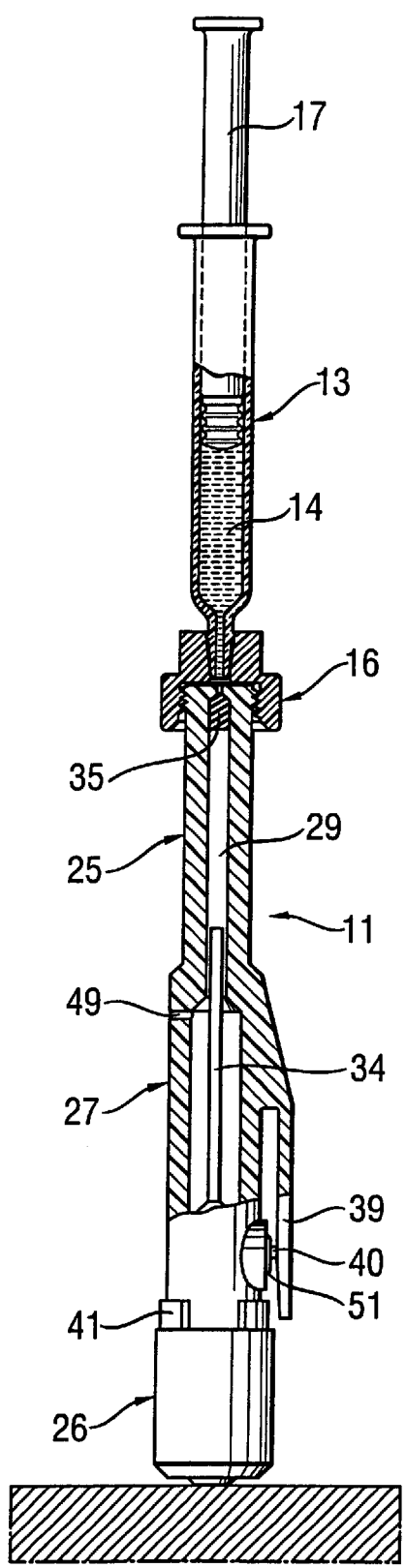
FIG. 3 shows a schematic representation of the connection of injector device 11 and the syringe 13 by means of the coupling member 16, before the syringe is operated for transferring the medication prefilled therein into the injector device 11.
Figure 4:
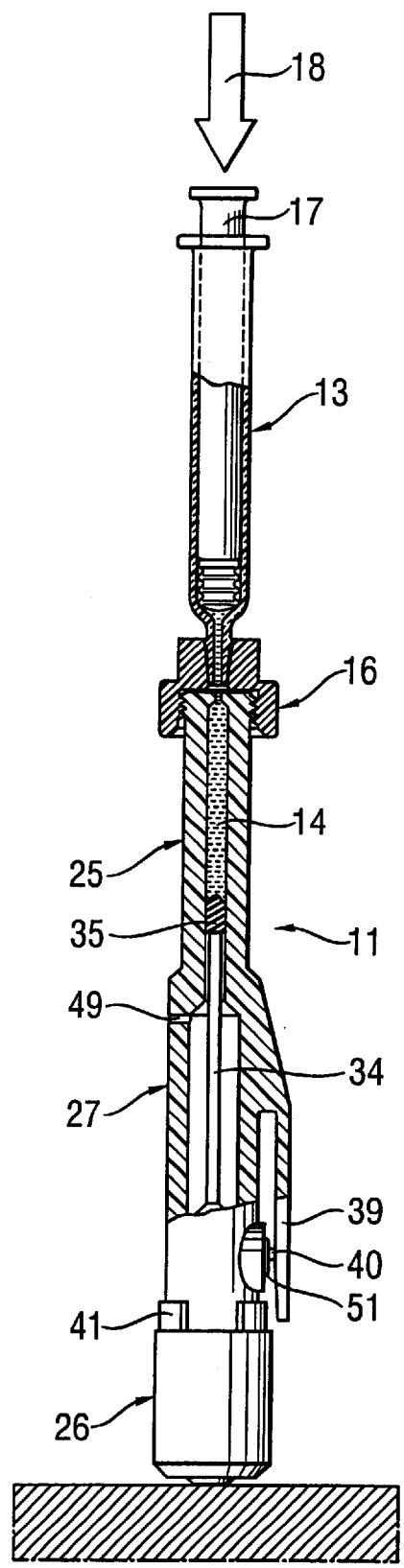
FIG. 4 shows a schematic representation of the connection of injector device 11 and the syringe 13 by means of the coupling member 16, after the syringe has been operated and the medication prefilled therein has been thereby transferred into the injector device 11.

The subject invention will now be described in terms of its preferred embodiments. These embodiments are set forth to aid the understanding of the invention, but are not to be construed as limiting.

FIG. 1 shows a schematic representation of a needleless injection system according to the invention. The system comprises the following components:

a needleless injector device 11 that is dimensioned and arranged as an integral unit to be grasped in the hand of a user, the device 11 having a barrel portion, a gas storage portion, and an intermediate portion extending between the barrel portion and the gas storage portion; and a syringe 13 prefilled with a medication 14, said syringe being suitable for loading the injector device 11 with said medication 14 prefilled in the syringe.

In a preferred embodiment an injection system according to the invention further comprises a coupling member or adapter 16 for connecting the prefilled syringe 13 to the needleless injector device 11 and thereby establishing a fluidic communication between the interior of the syringe 13 and the interior of the injector device 11 for the purpose of transferring a quantity of medication from the prefilled syringe 13 into the needleless.injector device 11.

As can be appreciated, in particular from FIG. 2, the coupling member or adapter 16 has a shape, which on one side matches the shape of an end part of the injector device 11 and on the opposite side matches the shape of the luer tip of the syringe 13, so that this tip can simply be plugged in that side of the coupling member or adapter 16. The side of the coupling member or adapter 16 which matches the shape of the injector device 11 is preferably adapted to be connected to that end part of the injector device 11 by a suitable mechanical connection, e.g. a screw or a bayonet type connection. As can be further appreciated, in particular from FIG. 2, the coupling member or adapter 16 has an inner shape which makes it possible to establish a fluidic communication between the interior of the injector device 11 and the interior of the syringe 13 when they are connected with each other by means of the coupling member or adapter 16.

In a preferred embodiment, coupling member or adapter 16 is preassembled with needleless injector device 11. This preassembled embodiment reduces the number of manipulations to be performed by the user and increases safety by reducing the risk of mismanipulation.

The components of an injection system according to the invention are preferably conserved in closed, suitable envelopes 12 and 15 respectively, which are only opened just before use of the components for their intended purpose.

The needleless injector device 11, which is schematically represented in the drawings of this patent application is for example of the type described in the above mentioned International Patent Application WO 89/08469. Injector device is described below under the section "Injector device" with reference to FIGS. 7 to 10. The barrel portion of the injector device 11 has a bore 29 for receiving medication to be injected by means of the injector device 11.

A preferred embodiment of a method according to the invention for administering a medication is described hereinafter in particular with reference to FIGS. 3 to 6.

To start with the user will of course first of all open the envelopes 12 and 15 and take therefrom the components of the injection system shown by FIG. 1. Then the user will screw the coupling member or adapter 16 on one end of the injector device 11 and he will plug the luer tip of the syringe 13 prefilled with a medication 14 into the coupling member or adapter 16. The resulting assembly of these components is shown by FIG. 3. It should be noted that this assembly establishes a fluidic communication between the interior of the syringe 13 and the interior of the injector device 11.

The next step is the transfer of the medication 14 prefilled in the syringe 13 into the bore 29 of the barrel portion of the injector device 11 through an aperture of that barrel portion. For this purpose the user presses the plunger 17 of the syringe 13 in the sense indicated by arrow 18 in FIG. 4 and thereby forces the medication to flow out of the syringe 13, through the coupling member or adapter 16 and into the barrel of the injector device 11. At the end of this step the barrel of the injector device 11 is thus loaded with medication 14.

The next step is the detachment of the syringe 13 from the injector device 11, for instance by unscrewing the coupling member or adapter 16 and thereby separating it from the injector device 11. FIG. 5 shows the syringe 13 and the coupling member or adapter 16 and FIG. 6 shows the injector device 11 after this operation.

After the step just described injector device 11 is ready to be operated in the way described in detail in the above mentioned International Patent Application WO 89/08469 for ejecting said medication 14 from the injector device and thereby pass the medication through the skin of the receiver of the injection.

A selected amount of medication injected in this way is preferably determined by the amount of medication 14 contained in the prefilled syringe 13. For this purpose, the entire amount of medication prefilled in the syringe 13 is transferred from the syringe 13 into the injector device 11, so that—in contrast to the known method of transfer described for example in the above mentioned International Patent Application WO 89/08469—no measuring of the amount of medication by the patient is necessary.

The prefilled syringe 13 and the injector device 11 are both apt to contain the same medication volume of e.g. 0.5 milliliter.

Injector Device

According to International Patent Application WO 89/08469 the structure and the operation of injector device 11 are as follows:

Generally, the device 11 includes an integral unit 24 that is dimensioned and arranged to be grasped in the hand of a user. It is integral in the sense that it carries its own one-shot power source instead of being reloadable and reuseable. As an idea of size, the unit 24 may be about ten or eleven centimeters long and about one and one-half centimeters across at its widest point. Of course, these dimensions are not critical.

Preferably composed of an injected molded thermoplastic material, the unit 24 includes a barrel portion 25, a gas storage portion 26, and an intermediate portion 27. The barrel portion extends from the intermediate portion 27 to a discharge end 28 of the barrel portion 25 and it defines a bore 29 (FIGS. 8–10) that extends from the intermediate portion 27 to an orifice or aperture 30 in the discharge end 28.

The gas storage portion 26 defines a gas storage compartment 31 in which is disposed a compressed gas such as $CO_2$. This may be introduced during manufacture by suitable means, such as through an opening that is then sealed with a plug, and the compressed gas is used as an energy source for injecting the selected dosage from the bore 29 through the aperture 30. In other words, it released from the storage compartment 31 to propel the selected dosage out of the barrel portion 29.

The intermediate portion 27 defines an expansion chamber or chamber 32 that is used for this purpose. Preferably, the chamber 32 is cylindrically shaped. The intermediate portion 27 and the chamber 32 extend between the gas storage portion 26 and the barrel portion 25, and a piston 33 combines with a pushrod 34 to couple force from compressed gas entering the chamber 32 to a plunger 35 disposed within the bore 29, the piston 26 having a size and shape conforming to the cross sectional size and shape of the chamber 32.

Injector device 11 includes gas release means for releasing the compressed gas from the compartment 31 so that the compressed gas can flow into the chamber 32. This is accomplished in the illustrated device 11 with a breakable member in the form of a hollow glass quill 36 that extends through the gas storage portion 26 as shown (FIG. 8), from an open end 37 in the storage compartment 31 a closed end 38 in the chamber 32. It may be suitably bonded in this position.

The gas release means so formed is actuated by breaking off the closed end 38 or the glass quill 36. Injector device 11 includes trigger means for enabling a user to actuate the gas release means, and this is accomplished in the device 11 with a trigger mechanism that includes a trigger 39 attached to the intermediate portion 27 for movement when depressed by the user. When depressed, a firing pin 40 presses against add breaks the fragile glass quill to release the compressed gas into the chamber 32. The gas flows from the storage compartment 31 through the hollow interior of the glass quill 36.

Figure 7:
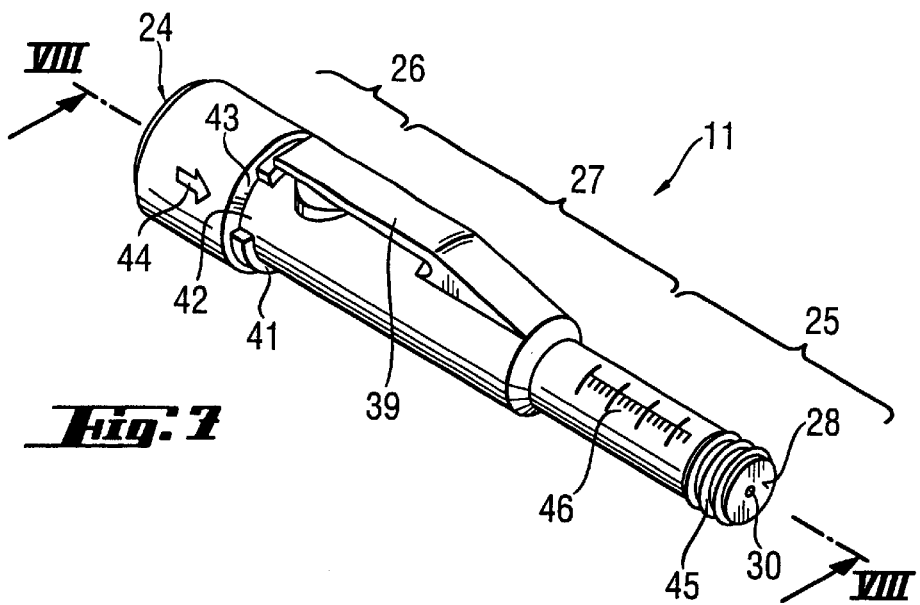
FIG. 7 shows a perspective view of a needleless injector device constructed according to the invention.

But in order to operate the trigger the user must first position a safety ring 41 (FIG. 7) in an off.position. The safety ring 41 circumscribes the intermediate portion 27 as shown in FIG. 7, and it is mounted for rotational movement so that a space 42 in the safety ring 41 can be moved into alignment with the trigger 39. This is the off position in which the trigger 39 can be depressed to fire the device 11, and it is indicated by alignment of a ridge 43 on the safety ring 41 with an indicator 44 provided for this purpose. The ridge also enhances user engagement of the safety ring 41.

Unless the safety ring 41 is in the off position, the trigger 39 is blocked from being depressed. The safety ring 41 is shown blocking the trigger 39 in FIGS. 7 and 8, and in the off position in FIGS. 9 and 10.

Operationally, the user grasps the device 11 and removes any sterility cover that might be provided over the discharge end 28, such as a cap member (not shown) that is arranged to be screwed onto a threaded end portion 45 of the barrel portion 25, for example. The threaded end portion 45 may employ a two-start thread that mates with threaded portions on the above described coupling member 16.

Figure 10:
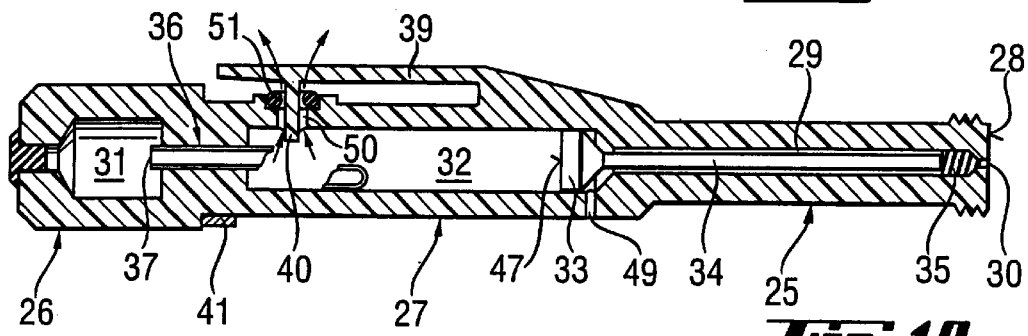
FIG. 10 shows another cross sectional view similar to FIG. 8 showing the injector device with the dosage fully injected, the trigger released, and the compressed gas discharging.

At this point in the operation, the plunger 35 is disposed fully forward in the bore 29 in the position shown in FIG. 10. Using the above described coupling member 16 and syringe 13 which form suitable dose dispenser means, the user loads a selected dosage of medication through the aperture 30 into the bore 29. This may be done with by attachment of coupling member 16 to the threaded end portion 45 of the barrel portion 25 (FIG. 7).

Figure 8:
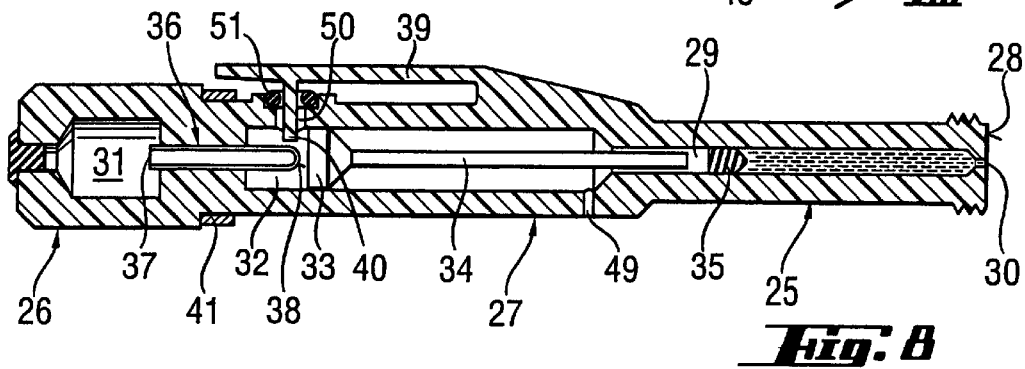

As the selected dosage is loaded into the bore 29, it forces the plunger 35 away from the discharge end 28 to a position such as that shown in FIG. 8. Preferably, at least a portion of the barrel portion 25 is sufficiently transparent to enable a user to visually discern the position of the plunger 35 relative to a plurality of graduations 46 provided on the barrel portion 25. This enables the user to ascertain precisely how much medication has been loaded into the bore 29 so that the loading procedure can be stopped as soon as the selected dosage has been loaded.

FIG. 8 shows a position the plunger 35 might occupied when loading has been completed, the stippling between the plunger 35 and the aperture 30 representing the selected dosage of medication that has been loaded into the bore 29.

At this point in the self-administration of the medication, the user turns the safety ring 41 to the off position. Next, the user places the discharge end 28 proximate the user's skin at a point where the medication is to be injected and depresses the trigger 39 to fire the device 11.

Figure 9:
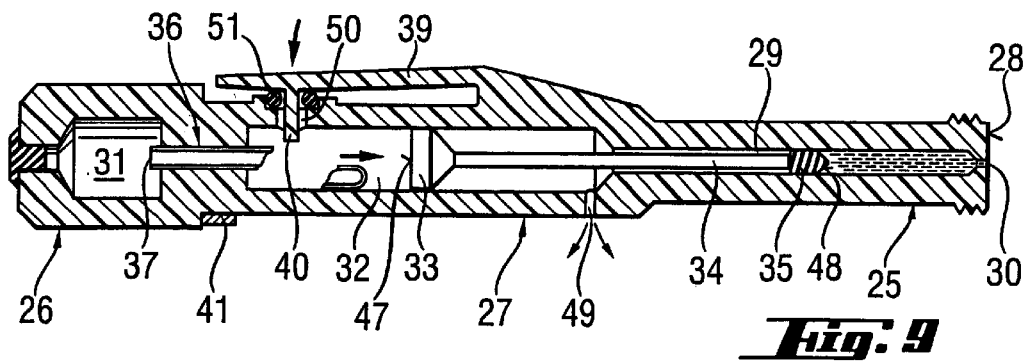
FIG. 9 shows another cross sectional view similar to FIG. 8 showing the injector device after firing with the safety off, the trigger depressed, and the dosage partially injected.

This results in the firing pin 40 breaking the glass quill 36 so that the compressed gas rushes through the quill 36 into the chamber 32 as shown in FIG. 9. In this regard, little transverse pressure is required to break the glass quill 36 so that a few ounces of pressure may be all that is needed to depress the trigger 39 sufficiently to fire the device 11.

As the compressed gas rushes into the chamber 32, it acts against a piston face 47 of the piston 33 (FIG. 9) and this drives the piston toward the bore 29 with the result that the pushrod 34 contacts the plunger 35 and drives it toward the aperture 30. This action causes a plunger face 48 of the plunger 35 to act against the medication and force it out of the aperture 30 in a high pressure jet depicted by the arrow extending outwardly from the aperture 30 in FIG. 9.

The plunger 35 may be composed of a rubber material, for example, and be configured conform to the bore cross section. Thus medication does not flow past the plunger 35 toward the piston 33. In addition, the plunger face 48 is configured as shown to conform to the shape of the bore 29 at the aperture 30 so that no medication remains in the bore 29 after firing.

According to one aspect of injector device 11, the piston face 47 has a larger surface area than the plunger face 48. This surface area differential results in more pressure being applied to the medication than the compressed gas applies to the piston face 47. This pressure amplification may be utilized to achieve an injection pressure at the aperture 30 of about 2,500–5,000 psi, for example, depending on the precise configuration employed, whereas the compressed gas might exhibit a pressure of about 840 psi at room temperature.

As the piston 33 moves toward the discharge end 30, gas ahead of the piston 33 (between the piston 33 and the barrel portion 25) vents through an opening 49 provided for this purpose (FIG. 9). Thus, the opening 49 serves as vent means disposed intermediate the piston 33 and the plunger 35 for enabling gas to escape from a region ahead of the piston 33.

After firing, the compressed gas discharges through a discharge port 50 provided around the firing pin 40 (FIG. 10). This may be a hole through which the firing pin 40 extends. However, the discharge port 50 is sealed momentarily when the user operates the trigger 39. This delays the escape of the compressed gas from the chamber 32 until the piston 33 has been driven substantially all the way to the fully fired position shown in FIG. 10.

The delay is accomplished by utilizing an O-ring seal 51 disposed in the position shown in FIGS. 8 and 10 so that when the trigger 39 is depressed, the trigger 39 presses against the seal 51 to seal the discharge port 50. The seal 51 may be composed of a know medical grade elastomeric material for this purposes. When the trigger 39 is released, it disengages the seal 51 to open or unseal the discharged port 50 so that the compressed gas can escape.

Other means may be used for delaying the escape of compressed gas through the discharge port 50. For example, a tapered firing pin may be provided along with a discharge port having a mating taper so that the firing pin wedges into the discharge port momentarily during firing.

Although preferred embodiments of the invention have been described using specific terms, such description is for illustrative purposes only, and it is to be understood that changes and variations may be made without departing from the spirit or scope of the following claims.

What is claimed is:

1. A coupling member comprising:
   (a) a first end configured and dimensioned to correspond to the shape of a discharge end of a needleless injector device;
   (b) a second end configured and dimensioned to correspond to and receive a luer tip of a syringe; and
   (c) an inner surface configured and dimensioned to establish a fluidic communication between an interior portion of the needleless injector device and an interior portion of the syringe,
      wherein said coupling member comprises a one-piece element integrally including means for forming a fluidically tight connection with said discharge end and said luer tip of said syringe.

2. The coupling member of claim 1, wherein the first end of the coupling member is adapted to be connected to the discharge end of the needleless injector device by a screw or bayonet type connection.

3. The coupling member of claim 1, wherein the second end of the coupling member is adapted to receive the luer tip of the syringe by a plug-in connection.

4. A kit comprising:
   (a) a needleless injection device having a body with a barrel portion and a discharge portion;
   (b) a syringe having a luer tip; and
   (c) a coupling member comprising:
      (i) a first end configured and dimensioned to correspond to the shape of and to be connected to the discharge end of the needless injector device;
      (ii) a second end configured and dimensioned to correspond to and receive the luer tip of the syringe; and
      (iii) an inner surface configured and dimensioned to establish a fluidic communication between an interior portion of the needleless injector device and an interior portion of the syringe,
         wherein said coupling member comprises a one-piece element integrally including means for forming a fluidically tight connection with said discharge end and said luer tip of said syringe.

5. The kit of claim 4, wherein the needleless injector device is an integral unit comprising:
   (a) a gas storage portion,
   (b) an intermediate portion extending between the gas storage portion and a barrel portion, and
   (c) the barrel portion which extends between the intermediate portion and a discharge end,
      wherein the barrel portion is configured and dimensioned to contain a bore extending between the intermediate portion and an aperture in the discharge end.

6. The kit of claim 4, wherein the needleless injector device is dimensioned and configured to be grasped in a hand of a user.

7. The kit of claim 4, wherein the end portion of the barrel portion of the needleless injector device is configured and dimensioned to be threaded.

8. The kit of claim 4, wherein the first end of the coupling member is adapted to be connected to the discharge end of the needleless injector device by a screw or bayonet type connection.

9. The kit of claim 4, wherein the second end of the coupling member is adapted to receive the luer tip of the syringe by a plug-in connection.

10. The kit of claim 4, wherein said coupling member is preassembled with said needleless injector device.

11. A method for parenterally administering a medication through the skin of an injection receiver, comprising:
   (a) providing a needleless injector device having a barrel portion, a gas storage portion, and an intermediate portion extending between the barrel portion and the gas storage portion;
   (b) providing a needleless syringe prefilled with a medication, said syringe being suitable for needleless loading of the injector device with said medication prefilled in the syringe;
   (c) loading the medication prefilled in the syringe into a bore of the barrel portion of the injector device through an aperture in the barrel portion thereof via a one piece coupling member, the one-piece coupling member including means for forming a fluidically tight connection with said aperture and a luer tip of said syringe, a dosage of the medication being thereby available in the injector device at the end of the loading;
   (d) detaching the prefilled syringe from the injector device; and
   (e) operating the loaded injector device to eject the dosage of medication contained therein from the injector device and thereby pass said dosage of the medication through the skin of an injection receiver.

12. A method according to claim 11, wherein the step of loading the medication into the injector device includes:

(a) connecting the prefilled syringe to the injector device; thereby establishing a fluidic communication between an interior portion of the syringe and an interior portion of the injector device; and (b) operating the prefilled syringe for transferring the entire amount of medication prefilled in the syringe from the syringe into the injector device.

13. A needleless injection system, comprising:

(a) a needleless injector device that is dimensioned and arranged as an integral unit to be grasped in the hand of a user, the device having a barrel portion with a bore for receiving medication to be injected, a gas storage portion, and an intermediate portion extending between the barrel portion and the gas storage portion;

(b) a syringe, having a luer tip, prefilled with a medication, said syringe being suitable for loading the injector device with said medication prefilled in the syringe; and (c) a coupling member for connecting the prefilled syringe to the needleless injector device and thereby establishing a fluidic communication between an interior portion of the syringe and the bore of the injector device for the purpose of transferring a quantity of said medication from the prefilled syringe into said bore of the injector device, wherein said coupling member comprises a one-piece element integrally including means for forming a fluidically tight connection with an aperture of said bore of the injector device and said luer tip of said syringe.

14. A system according to claim 13 further comprising coupling means for connecting the prefilled syringe to the needleless injector device and thereby establishing a fluidic communication between the interior of the syringe and the interior of the injector device for the purpose of transferring a quantity of medication from the prefilled syringe into the needleless injector device.

* * * * *

UNITED STATES PATENT AND TRADEMARK OFFICE
CERTIFICATE OF CORRECTION

PATENT NO.    : 6,599,264 B1
DATED         : July 29, 2003
INVENTOR(S)   : Werner Erni and Martin List It is certified that error appears in the above-identified patent and that said Letters Patent is hereby corrected as shown below:

Column 8,
Line 5, delete "discharge end of the needless injector device;" and insert -- discharge end of the needless injector device; --.

Column 10,
Lines 12-18, delete claim 14 in its entirety.

Signed and Sealed this

Twenty-seventh Day of April, 2004

JON W. DUDAS
*Acting Director of the United States Patent and Trademark Office*